United States Patent [19]

Ranade

[11] Patent Number: 4,482,733

[45] Date of Patent: Nov. 13, 1984

[54] PROCESS OF MANUFACTURING DIARYL ESTERS OF DICARBOXYLIC ACIDS

[75] Inventor: Gautam R. Ranade, Grand Island, N.Y.

[73] Assignee: Occidental Chemical Corporation, Niagara Falls, N.Y.

[21] Appl. No.: 422,794

[22] Filed: Sep. 24, 1982

[51] Int. Cl.$^3$ .............................................. C07C 67/08
[52] U.S. Cl. ................................. 560/86; 260/455 R; 560/11; 560/18; 560/21; 560/37; 560/52; 560/73; 560/85; 568/15; 203/DIG. 6
[58] Field of Search .............. 260/455 R; 560/37, 21, 560/52, 73, 86, 85, 204, 11, 18; 568/15; 203/DIG. 6

[56] References Cited

U.S. PATENT DOCUMENTS

| | | | |
|---|---|---|---|
| 3,356,712 | 12/1967 | Renckhoff et al. | 560/86 |
| 3,389,164 | 6/1968 | Renckhoff et al. | 560/86 |
| 3,413,336 | 11/1968 | Hulsmann et al. | 560/86 |
| 3,471,549 | 10/1969 | Hulsmann et al. | 560/86 |
| 3,772,389 | 11/1973 | Lowrance | 560/86 |

*Primary Examiner*—Natalie Trousof
*Assistant Examiner*—Vera C. Clarke
*Attorney, Agent, or Firm*—James F. Tao

[57] ABSTRACT

An improved process for preparing diaryl esters of dicarboxylic acids is disclosed, in which the esterification reaction is optimized by gradually increasing the temperature at which the reaction is being conducted according to a predetermined pattern. The temperature increase should be a function of the degree of esterification. The diaryl esters so prepared are useful in making linear polyesters.

10 Claims, 1 Drawing Figure

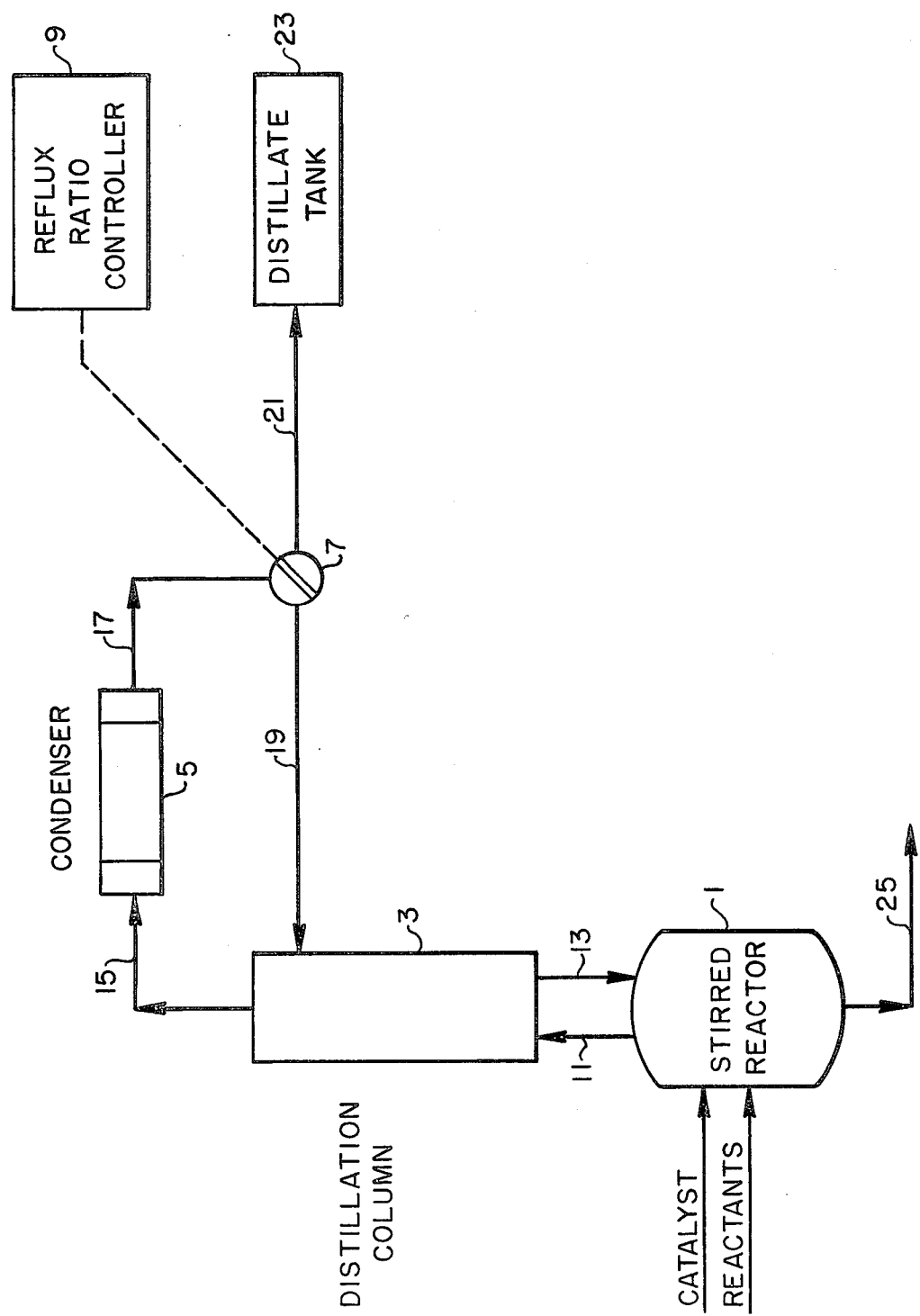

PROCESS OF MANUFACTURING DIARYL ESTERS OF DICARBOXYLIC ACIDS

BACKGROUND OF THE INVENTION AND PRIOR ART STATEMENT

This invention relates to an improved process for making esters. More particularly, the invention relates to an economical and efficient process for accelerating the rate of esterification in which dicarboxylic acids or their esters and monohydroxy aromatic compounds are reacted to form esters.

Linear polyesters which are essentially the product of reaction of a bisphenol and dicarboxylic acids are important thermoplastic materials due to their excellent performance at high temperatures. It is known to produce such linear polyesters by first reacting at least one dicarboxylic acid with a monohydroxy aromatic compound to form a diaryl ester of the dicarboxylic acid, and then carry out a transesterification polymerization between the diaryl ester and a bisphenol. See, e.g., British Pat. No. 924,607 and U.S. Pat. Nos. 4,255,555 and 4,319,017. However, those references are primarily concerned with transesterification reaction for preparing the linear polyesters.

Significant commercial interest in recent years has developed in the field of phenolic esters of aromatic dicarboxylic acids, such as diphenyl isophthalate and diphenyl terephthalate, due to their use in many processes. For example, the mixtures of diphenyl isophthalate and diphenyl terephthalate can be reacted by melt polycondensation with 4,4'(1-methyl-ethylidene) bis(phenol) to produce aromatic polyesters or polyarylates. Diphenyl phthalates can also be reacted with primary amines in a solvent to make polyamides. Likewise, 3,3' diaminobenzidene may be condensed with various diphenyl esters to form polybenzimidazoles.

The prior art processes for preparing the diaryl esters suffer from a number of disadvantages. To obtain a degree of esterification in excess of 90%, which is demanded by the economics of the processes, the prior art processes require lengthy reaction times. Diaryl esters substantially free of dicarboxylic acids may also be required for the production of high quality linear polyesters. Other disadvantages include a requirement for high reaction temperatures, i.e. in the range of 280°-300° C., for prolonged periods. Such relatively high temperatures not only consume more energy than reactions conducted at lower temperatures, but they also result in a darker colored product which may be contaminated with by-products from side reactions. Other prior art processes also utilize pressures in excess of 100 psig and approaching 200 psig, which is again more costly and increases safety hazards.

U.S. Pat. No. 4,124,566 discloses a process for preparing polyesters in which the first step is the esterification of a difunctional carboxylic acid with an aromatic monohydroxy compound and an aliphatic diol and/or a dihydroxybenzene. The esterification reaction is to be performed in the presence of an aromatic hydrocarbon medium. This disclosure of the use of a small portion of aromatic esters as solvent for the reaction as well as the use of an azeotrope, including aromatic hydrocarbons such as ethyl benzene, affords some relief from lengthy reaction cycles and low conversion rates. However, the addition of the aromatic esters in the esterification reaction mixture reduces the volume available for the reaction and, consequently, reduces yield per batch. The addition of an azeotropic agent also dilutes the reaction mixture, and it may adversely affect the solubility of the dicarboxylic acid in the mixture. The use of an azeotropic agent such as ethyl benzene or xylene also increases the potential for fire and explosion, and the added danger of environmental health hazards to workers exposed to the atmosphere. Thus, the use of such aromatic hydrocarbons requires careful monitoring and treatment to prevent contamination of the environment. Accordingly, there is a need for an improved process for making diaryl esters of dicarboxylic acids.

Other prior art found in a search includes U.S. Pat. Nos. 3,356,712; 3,389,164; 3,413,336; 3,442,868; 3,471,549; 3,694,490; 3,833,643; and 4,271,311. None of these patents are believed to be relevant to the present invention.

It is, therefore, an object of the invention to provide improved process for making diaryl esters of dicarboxylic acids.

It is another object of the present invention to provide an economical and environmentally safe process for making diaryl esters which permits relatively short reaction times and high conversion rates while operating at relatively low reaction temperatures and pressures.

These and other objects of the invention can be gathered from the following disclosure.

SUMMARY OF THE INVENTION

In accordance with the present invention, there is provided a process for the esterification of at least one dicarboxylic acid with a monohydroxy aromatic compound, in which the dicarboxylic acid is represented by the formula:

$$R_1X-\overset{O}{\underset{\|}{C}}-(Z)_n-\overset{O}{\underset{\|}{C}}-XR_2$$

in which X is oxygen or sulfur, Z is alkylene, —Ar— or —Ar—Y—Ar— where Ar is aromatic, Y is alkylene of 1 to 10 carbon atoms, haloalkylene, $$-O-, -SO-, -SO_2-, -SO_3-, -CO-, G\overset{|}{P}=O \text{ or } GN=,$$

and G is alkyl, haloalkyl, aryl, haloaryl, alkylaryl, haloalkylaryl, arylalkyl, haloarylalkyl, cycloalkyl and halocycloalkyl, n is 0 or 1, and $R_1$ and $R_2$ are independently selected from the group consisting of hydrogen and lower alkyl. The esterification reaction is carried out at a temperature between about 220° C. and about 300° C., preferably in the presence of a catalyst, while continuously removing a by-product of the esterification reaction comprising water and/or lower alkyl alcohol(s). Surprisingly, the applicant has found that the esterification reaction can be conducted at a relatively lower temperatures and yet achieve high conversion rates over short reaction times by the use of reaction temperature which is increased during the course of the esterification reaction according to a predetermined pattern. Generally, the reaction temperature should be increased as a function of the degree of esterification. The preferred functional relationship between reaction temperature and the degree of esterification or percent completion of esterification is given in a table below. In this way, the degree of esterification or completion of reaction is maximized, the reaction pressure reduced, and the resultant ester product's exposure to high temperature also reduced.

BRIEF DESCRIPTION OF THE DRAWING

In the drawing, a simple reactor system for carrying out the esterification reaction in accordance with the present invention is shown. A stirred reactor vessel 1 equipped with a distillation means 3 and condenser means 5 is operated with a reflux splitter 7, which is controlled by a reflux ratio controller 9. In operation, a charge of the reactants made of a mixture of the dicarboxylic acid(s) and the monohydroxy aromatic compound is charged into the reaction vessel 1 through inlet means (not shown). Advantageously, a catalyst is also charged into the reaction vessel 1 to assist the esterification reaction. The reaction vessel 1 is equipped with a heating means and a temperature sensing means (both not shown). The heating means may be controlled in conjunction with the temperature sensing means to maintain the mixture within reaction vessel 1 at the predetermined temperature. As the esterification reaction proceeds, water and/or alcoholic by-products are produced in reaction vessel 1 and are vaporized at the reaction temperature and passed to the distillation means 9 through connecting means schematically represented by line 11. The return from distillation means to reaction vessel 1 is schematically represented by line 13. Distillation means 3 may be any of the known distillation devices, for example, bubble cap tray columns or packed towers. The overhead 15 from distillation means 9 is conducted to condenser means 5 and cooled there by a cooling medium such as water into a liquid condensate stream 17. Condensate 17 is split into two streams by a reflux splitter 7, which is controlled by the reflux ratio controller 9. The condensate stream 17 is split into a liquid return stream 19 and a distillate stream 21. The distillate stream 21 is passed to a distillate tank 23 for storage. The liquid return stream 19 is passed back to the top of the distillation means 9. Using the letter L to denote the moles of liquid return stream 19 and D to represent the moles of distillate stream 21, the Reflux Ratio is defined as the fraction L/D. The diaryl esters produced, together with unreacted reactants, are withdrawn from the reaction vessel 1 through line 25.

DETAILED DESCRIPTION OF THE INVENTION

As indicated above, the present invention provides an improved process for preparing diaryl esters, which are useful in the preparation of linear polyesters, by the reaction of at least one dicarboxylic acid or its ester with a monohydroxy aromatic compound. The dicarboxylic acids which are useful in the process of the invention are known and they can be represented by the formula:

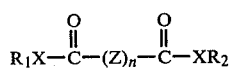

in which X is oxygen or sulfur, Z is alkylene, —Ar— or —Ar—Y—Ar— where Ar is aromatic, Y is alkylene of 1 to 10 carbon atoms, haloalkylene,

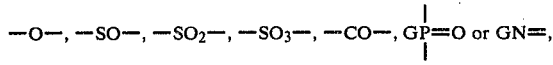

and G is alkyl, haloalkyl, aryl, haloaryl, alkylaryl, haloalkylaryl, arylalkyl, haloarylalkyl, cycloalkyl and halocycloalkyl, n is 0 or 1, and $R_1$ and $R_2$ are independently selected from the group consisting of hydrogen and lower alkyl. Examples of aromatic and aliphatic dicarboxylic acids are disclosed in U.S. Pat. No. 4,126,602, and include: aromatic dicarboxylic acids such as phthalic acid, isophthalic acid, terephthalic acid, bis(4-carboxyl)-diphenyl, bis(4-carboxyphenyl)ether, bis(4-carboxyphenyl)-sulfone, bis(4-carboxyphenyl-carbonyl, bis(4-carboxyphenyl)-methane, bis(4-carboxyphenyl)-dichloromethane, 1,2- and 1,1-bis(4-carboxyphenyl)-ethane, 1,2- and 2,2-bis(4-carboxyphenyl)-propane, 1,2- and 2,2-bis(3-carboxyphenyl)-propane, 2,2-bis(4-carboxyphenyl)-1,1-dimethyl propane, 1,1- and 2,2-bis(4-carboxyphenyl)-butane, 1,1- and 2,2-bis(4-carboxyphenyl-pentane, 3,3-bis-(4-carboxyphenyl)-heptane, 3,3-bis(3-carboxyphenyl)-heptane; and aliphatic acids such as oxalic acid, adipic acid, succinic acid, malonic acid, sebacic acid, glutaric acid, azelaic, suberic acid and the like. Isophthalic acid and terephthalic acid are the preferred dicarboxylic acids for use in the process of the present invention, due to their easy availability and low cost. More preferably, the dicarboxylic acid employed in the esterification reaction comprises a mixture of about 60 to about 100 mole percent isophthalic acid and about 40 to about 0 mole percent terephthalic acid. Most preferably, the dicarboxylic acid component is made of a mixture of about 75 to about 85 mole percent isophthalic acid and about 25 to about 15 mole percent terephthalic acid.

The monohydroxy aromatic compounds for use in the process in the present invention is also known. Generally, they may be of the benzene or naphthalene series containing 6 to 20 carbon atoms. Examples of such monohydroxy aromatic compounds include phenol, o-, m-, or p-cresol, xylenol, a halophenol such as p-chlorophenol, 3,5-dibromophenol, a nitrophenol such as o-, m- or p-nitrophenol, 1-naphthol, 2-naphthol, 1-hydroxy-4-methyl naphthlene, and the like.

The dicarboxylic acid useful in the reaction of the present process include both aliphatic and aromatic acids as well as their respective esters. The rate of conversion may be enhanced when using mixtures of the acids or esters by increasing the proportions of the more soluble acid or ester in monohydroxy aromatic compounds over the less soluble acid or ester. In determining the exact proportion of acids to be used, consideration should be given to the properties of the esters produced and the effect they may have on the linear polyesters produced therefrom. When using mixtures of isophthalic and terephthalic acids, normally the isophthalic acid content will be increased up to the point where no significant change in polymer properties or processing characteristics are observed.

A molar excess of monohydroxy aromatic compound is preferably used in the reaction with the dicarboxylic acid to facilitate the completion of the esterification reaction. Although a molar ratio of the monohydroxy aromatic compound to the dicarboxylic acid of about 2:1 may be used, it is preferred that such molar ratio be from about 3:1 to about 10:1. More preferably, such molar ratio employed should be from about 4:1 to about 8:1.

The temperature to be employed in esterification process of the invention may be varied, and it depends on the reactants employed. Generally, temperatures should be between about 220° to 300° C. As indicated above, the present invention provides that the reaction temperature should be gradually increased during the course of the esterification reaction. This will be more fully described below. The pressure employed in the present process is determined by the temperature, the particular reactants employed, and other operating conditions. Generally, the pressure in the reaction vessel is substantially below 100 psig. Due to the relative molecular weights of water and the monohydroxy aromatic compound and their vapor pressures, a small amount of water in the reactants may cause the initial pressure in the reactor to be somewhat higher than indicated herein.

As indicated above, a catalyst is preferably used in the esterification reaction. These catalysts are known in the art. See, e.g., U.S. Pat. No. 4,124,566. Examples of the catalysts are elemental metals such as sodium, potassium, lithium, calcium, magnesium, barium, tin, strontium, zinc, iron, aluminum, cobalt, lead, nickel, titanium, magnesium, antimony or arsenic, and compounds of these metals such as their oxides, hydrides, hydroxides, halides, inorganic acid salts, organic acid salts, complex salts, double salts, alcoholates, or phenolates. Of these, titanium compounds such as titanium tetrabutoxide, titanium oxalate or titanium oxide, tin compounds such as dibutyltin oxide, antimony compounds such as antimony trioxide, and lead compounds such as lead oxide are preferred. I have found that organic titanium compounds, such as certain aliphatic esters of ortho titanic acid, are especially effective catalysts. Examples of aliphatic esters of ortho titanic acids include tetrabutyl titanate, tetraisopropyl titanate or tetraoctylene glycol titanate. Some of these organic titanium catalysts are available from the duPont Company under its trademark Tyzor. The amount of the catalyst to be used is also known in the art, and it is usually between about 0.001 to about 5 mole percent based on the amount of the dicarboxylic acid employed.

In the process of the present invention, the temperature of the reaction mixture is initially brought up to the reaction level, generally about 220°-230° C. Thereafter, the reaction temperature is gradually increased until the esterification reaction is substantially complete, when the temperature will be about 290° C. or slightly below. The degree of esterification or the completeness of the reaction will generally be substantially above 90%. In most instances, the percent completion of reaction will be 95% or above.

As indicated above, the temperature of the reaction mixture should be quickly brought up to the reaction level, i.e. about 220°-230° C., and then gradually increased as the reaction proceeds towards completion. I have found that the following temperature profile to be optimum in the practice of the process according to the invention:

| % Completion of Reaction | Temperature °C. |
| --- | --- |
| 0-20 | 220-240 |
| 21-40 | 225-245 |
| 41-60 | 230-255 |

-continued

| % Completion of Reaction | Temperature °C. |
| --- | --- |
| 61-80 | 240-260 |
| 81-100 | 250-300 |

As will be seen from the examples given below, the controlled increase of the reaction temperature in accordance with the present invention results in high conversion rates, low reaction pressures, and reduced exposure of the ester product to the relatively higher temperatures necessary when the reaction approaches completion. The advantages of conducting the reaction at relatively lower pressures are known to those skilled in the art. The lower pressures permit the use of less expensive reaction devices, make the separation of by-products easier, and poses less danger to operating personnel. The reduced exposure of the ester product to the relatively high temperatures necessary towards the end of the reaction protects the ester product from degradation and dark coloring. The reduced exposure to high temperatures also minimizes undesirable side reactions and by-products. The reduced reaction temperature necessary during much of the reaction time is also energy efficient.

The process of the present invention may be practiced in conjunction with the process of making diaryl esters of dicarboxylic acids, disclosed in my co-pending application, concurrently filed herewith. In said co-pending application, it is disclosed that the esterification reaction may be optimized by removing water and other by-products of the reaction according to a predetermined pattern. This is done, according to the disclosure of said co-pending application, by varying the reflux ratio in the distillation means according to the following profile:

| % Completion of Reaction | Reflux Ratio |
| --- | --- |
| 0-25 | 1-5 |
| 26-50 | 3-10 |
| 51-80 | 5-15 |
| 81-100 | 7-20 |

Most preferably, the reflux ratio is varied according to the following profile:

| % Completion of Reaction | Reflux Ratio |
| --- | --- |
| 0-25 | 2-5 |
| 26-50 | 5-7 |
| 51-80 | 7-10 |
| 81-100 | 10-15 |

The process according to the invention may be carried out, in its simplest form, in a batch-wise manner as illustrated in the drawing, or it may be carried out in a more or less continuous manner, by having a plurality of reactors operating in stages. The reaction also may be carried out in a modified batch manner, such as by intermittantly adding the monohydroxy aromatic compound to the reactor in the earlier part of the reaction period.

The invention will now be further illustrated by the following Examples.

EXAMPLE 1

The reaction apparatus consisted of a 50 gallon jacketed pressure reactor having an agitator-baffle assembly. The reactor was electrically heated, and it had a temperature control device. The reactor was equipped with a packed distillation column, a shell and tube condenser, a reflux splitter and a reflux ratio controller combination.

The reactor was charged with 54.6 parts by weight of isophthalic acid, 18.2 parts by weight of terephthalic acid, and 210 parts by weight of phenol. Two mole percent (based on total acid charge) of antimony oxide catalyst was also charged to the reactor. The reaction system was closed and heated to a temperature of about 230° C., from which point the reaction time was counted. The temperature in the reactor system was gradually increased to 288° C. according to the profile shown in Table 1 below.

TABLE 1

| Time (hrs.) | Temperature °C. | Pressure, psig | Degree of Esterification, % |
|---|---|---|---|
| 0 | 230 | 46 | — |
| 2 | 250 | 46 | 70.7 |
| 4 | 252 | 43 | 80.9 |
| 6 | 265 | 43 | 94.4 |
| 8 | 288 | 45 | 96.4 |

A reflux ratio of 20:1 was used throughout the entire reaction period. The average rate of distillate collection was about 12 parts by weight per hour. The pressure in the reactor system reached a maximum of about 54 psig after approximately 1.5 hours of reaction. Samples were obtained from the reactor at regular intervals and were analyzed for acid number (AN) and phenol content. The acid number (AN) is defined as the amount in milligrams of potassium hydroxide needed to completely neutralize one gram of the sample by titration method. The corrected acid number ($AN_c$) was calculated by using the following equation:

$$AN_c = \frac{AN}{1 - Wp} \quad (1)$$

in which Wp represents the weight fraction of phenol in the sample. The degree of esterification (DE) was calculated by using:

$$DE = \frac{1 - \frac{(AN_c)(Ma)}{2(56,100)}}{1 + Ec(AN_c)\frac{Ma}{2(56,100)}} \times 100 \quad (2)$$

in which $$Ec = \frac{Me - Ma}{Ma},$$

and Ma and Me represent the molecular weights of the acid and of the ester, respectively.

EXAMPLE 2

The procedure of Example 1 was repeated, except that the time-temperature profile was changed to that shown in Table 2 below.

TABLE 2

| Time (hrs.) | Temperature °C. | Pressure, psig | Degree of Esterification, % |
|---|---|---|---|
| 0 | 230 | 41 | — |
| 2 | 283 | 112 | 73.6 |
| 4 | 287 | 74 | 80.3 |
| 6 | 288 | 56 | 93 |
| 8 | 288 | 21 | 96.5 |

The pressure in the reactor reached a maximum of 120 psig after approximately 45 minutes of reaction. Although approximately the same degree of esterification was achieved using this temperature profile, as compared to that of Example 1, the maximum pressure in the reactor system was much higher in this example—almost twice the pressure of Example 1. Aside from the fact that the higher pressure required the use of apparatus that will be able to withstand the pressure, it is well known that separation processes such as distillation are more difficult to accomplish at higher pressures rather than lower pressures. In addition, it can be seen that the ester product was exposed to the relatively higher temperatures of more than 280° C. for a much longer period of time under the present example as compared to the conditions in Example 1. The higher temperatures tend to cause the ester products to turn to darker color, which is undesirable. Also undesirable by-products tend to be formed thereby.

EXAMPLE 3

The procedure of Example 1 was repeated, and the reactor was charged with 37.5 parts by weight of isophthalic acid, 12.5 parts by weight of terephthalic acid, and 170 parts by weight of phenol. Two mole percent of antimony oxide catalyst, based on the total acid charge, was added to the reactor. The reactor system was then closed and heated until 230° C. was reached. The temperature in the reactor was then increased according to the following profile:

TABLE 3

| Time (hrs.) | Temperature °C. | Pressure, psig. | Degree of Esterification, % |
|---|---|---|---|
| 0 | 230 | 32 | — |
| 1 | 241 | 47 | — |
| 2 | 246 | 46 | 75 |
| 3 | 260 | 55 | 87 |
| 4 | 270 | 58 | 93 |
| 5 | 278 | 49 | 96 |
| 6 | 287 | 48 | 98 |

The maximum pressure in the reactor was 58 psig, reached after four hours of reaction. It may be noted that the final degree of esterification, or the completeness of the reaction, was somewhat better than those obtained in Examples 1 and 2 even though the reaction time was only six hours as compared to the eight hours for the other two examples.

The present application is being concurrently filed with applicant's co-pending application Ser. No. 422,792 and Ser. No. 422,793, both for Process of Manufacturing Diaryl Esters of Dicarboxylic Acids, the disclosures of which are incorporated herein by reference.

The invention has been described with reference to particular and preferred embodiments thereof. It is to be understood that various changes and modifications can be made without departing from the spirit and scope of the invention.

What is claimed is:

1. A process for preparing esters which comprises reacting a monohydroxy aromatic compound with at least one dicarboxylic acid in a reactor having a distillation means, said acid being represented by the formula:

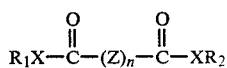

wherein X is oxygen or sulfur, Z is alkylene, —Ar— or —Ar—Y—Ar— wherein Ar is aromatic, Y is alkylene of 1 to 10 carbon atoms, haloalkylene,

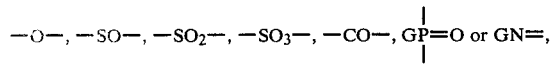

and G is alkyl, haloalkyl, aryl, haloaryl, alkylaryl, haloalkylaryl, arylalkyl, haloarylalkyl, cycloalkyl and halocycloalkyl, n is 0 or 1, and $R_1$ and $R_2$ are independently selected from the group consisting of hydrogen and lower alkyl, continuously removing a by-product of said reaction comprising water and/or lower alkyl alcohol(s) through said distillation means, said reaction being conducted at a temperature between about 220° C. and about 300° C., said temperature being increased within said range during the course of the reaction according to a predetermined pattern.

2. A process according to claim 1 wherein said distillation means being operated at a reflux ratio between about 1 to about 20, said reflux ratio being periodically increased according to a predetermined pattern as the esterification reaction proceeds towards completion.

3. A process according to claim 2 wherein said reflux ratio is varied according to the following profile:

| % Completion of Reaction | Reflux Ratio |
|---|---|
| 0–25 | 2–5 |
| 26–50 | 5–7 |
| 51–80 | 7–10 |
| 81–100 | 10–15 |

4. A process according to claim 1 wherein said temperature being increased from about 230° C. to about 290° C.

5. A process according to claim 1 wherein the pressure in said reactor is about 30 to about 70 psig.

6. A process according to claim 1 wherein said temperature is varied according to the following profile:

| % Completion of Reaction | Temperature °C. |
|---|---|
| 0–20 | 220–240 |
| 21–40 | 225–245 |
| 41–60 | 230–255 |
| 61–80 | 240–260 |
| 81–100 | 250–300 |

7. A process according to claim 3 wherein said temperature is varied according to the following profile:

| % Completion of Reaction | Temperature °C. |
|---|---|
| 0–20 | 220–240 |
| 21–40 | 225–245 |
| 41–60 | 230–255 |
| 61–80 | 240–260 |
| 81–100 | 250–300 |

8. A process according to claim 5 wherein said temperature is varied according to the following profile:

| % Completion of Reaction | Temperature °C. |
|---|---|
| 0–20 | 220–240 |
| 21–40 | 225–245 |
| 41–60 | 230–255 |
| 61–80 | 240–260 |
| 81–100 | 250–300 |

9. A process according to claim 1 wherein said dicarboxylic acid comprises isophthalic acid, terephthalic acid, and mixtures of isophthalic and terephthalic acids, and wherein said monohydroxy aromatic compound is phenol, a halo-phenol, or a nitro-phenol.

10. A process according to claim 7 wherein said dicarboxylic acid comprises isophthalic acid, terephthalic acid, and mixtures of isophthalic and terephthalic acids, and wherein said monohydroxy aromatic compound is phenol, a halo-phenol, or a nitro-phenol.

* * * * *